United States Patent
Ohtsuki et al.

(10) Patent No.: US 6,355,266 B1
(45) Date of Patent: Mar. 12, 2002

(54) TRANSDERMAL ABSORPTION PREPARATION

(75) Inventors: Tomohiro Ohtsuki; Chikako Kiuchi; Yoshiko Yoshino, all of Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/529,490

(22) PCT Filed: Oct. 14, 1998

(86) PCT No.: PCT/JP98/04649

§ 371 Date: Apr. 14, 2000

§ 102(e) Date: Apr. 14, 2000

(87) PCT Pub. No.: WO99/18955

PCT Pub. Date: Apr. 22, 1999

(30) Foreign Application Priority Data

Oct. 15, 1997 (JP) .............................................. 9-281658

(51) Int. Cl.[7] .................................................. A61K 9/70
(52) U.S. Cl. ........................................ 424/449; 424/448
(58) Field of Search ................................. 424/448, 449

(56) References Cited

U.S. PATENT DOCUMENTS 4,474,798 A  10/1984  Inagi et al. .................. 424/274

FOREIGN PATENT DOCUMENTS

| EP | 0 055 029 | 6/1982 |
| JP | 57-98209 | 6/1982 |
| JP | 58-189115 | 11/1983 |
| WO | WO95/20567 | * 8/1995 |

OTHER PUBLICATIONS

Nobuyoshi Kaneniwa et al., "Mechanism of Dissolution of Indometacin Crystal Polymorph", Journal of the Pharmaceutical Society of Japan (Yakugaku Zasshi), (1987), 107(4), pp. 308–314.

Chemical Abstracts, vol. 109, Abstract No. 215911 & Ramtoola, Z. et al., Drug Dev. Ind. Pharm., (1988), 14(15–17), pp. 2241–2253.

Teruyoshi Yokoyama et al., "Studies on Drug Nonequivalence. IX. Relationship between Polymorphism and Rectal Absorption of Indomethacin", Journal of the Pharmaceutical Society of Japan (Yakugaku Zasshi), (1979), 99(8), pp. 837–842.

* cited by examiner

Primary Examiner—Jose' G. Dees
Assistant Examiner—Michael A. Williamson
(74) Attorney, Agent, or Firm—Sughrue Mion, PLLC

(57) ABSTRACT

A transdermal absorption preparation containing α-form crystals of indomethacin in a vehicle. The present invention aims to provide an indomethacin-containing transdermal absorption preparation increased in the percutaneous absorption of indomethacin from the preparation, and improved in the stability of indomethacin in the preparation.

3 Claims, 3 Drawing Sheets

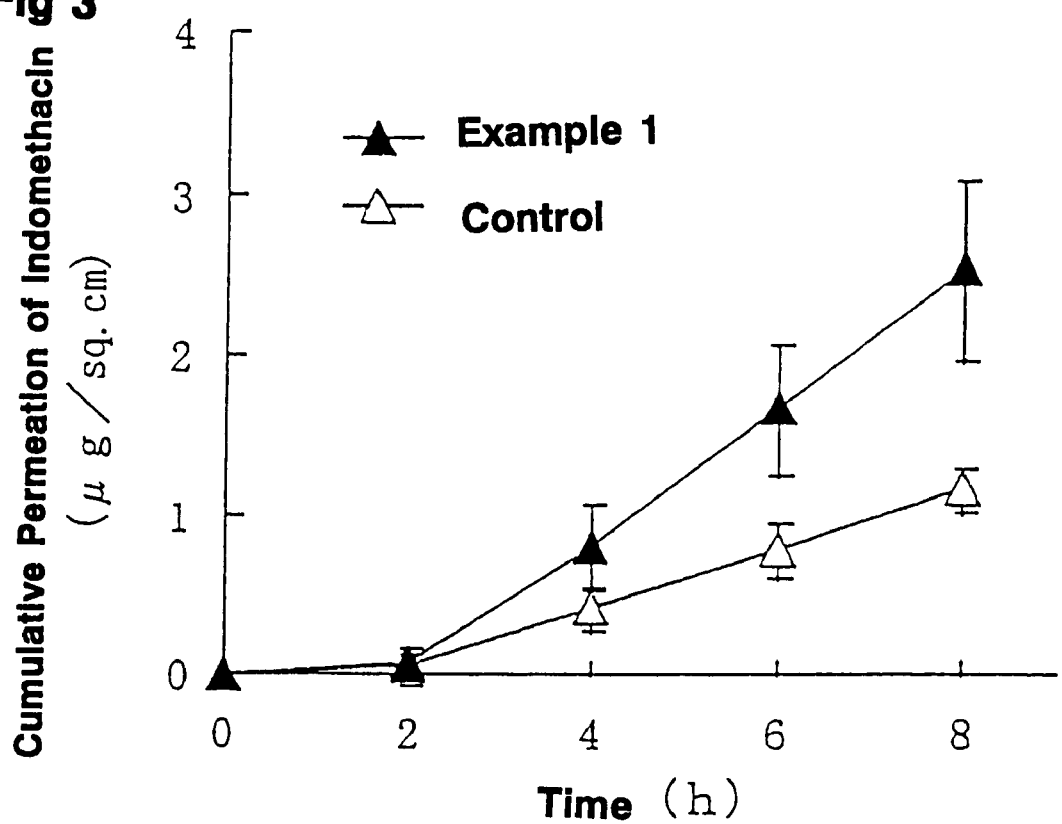

TRANSDERMAL ABSORPTION PREPARATION

TECHNICAL FIELD

The present invention relates to an indomethacin-containing transdermal absorption preparation.

BACKGROUND ART

Preparations for external use, containing anti-inflammatory analgesics, such as indomethacin more effective than salicylic drugs, have been used as one of therapeutic drugs in the treatment of pain due to contusion, sprain or muscular fatigue, and pain associated with shoulder stiffness. These preparations have been useful in that they diminish systemic adverse reactions because of topical administration. However, the percutaneous absorption of indomethacin is not sufficient, so that indomethacin-containing transdermal absorption preparations hitherto used have been solutions. The solution type indomethacin is easily hydrolyzable and lacks stability.

Indomethacin exists as α-form (needle-like), β-form, or γ-form (platy) crystals because of polymorphism. The γ-form is known as a stable form and the α-form as a meta-stable form. The conventional commercially available transdermal indomethacin preparations have contained the solution type indomethacin or the γ-form crystals, and there have been no transdermal indomethacin preparations containing α-form crystals. Rectal absorption from suppositories containing α-form crystals of indomethacin has been reported to be better than that from suppositories containing γ-form crystals (T. Yokoyama, Journal of the Pharmaceutical Society of Japan, 99, 837–842, 1979), but there have been no studies of the absorption of transdermal absorption preparations containing α-form crystals of indomethacin. Nor have there been any reports of the relationship between the crystal form of indomethacin and the stability of indomethacin in its preparations for external use.

It is an object of the present invention to provide an indomethacin-containing transdermal absorption preparation increased in the percutaneous absorption of indomethacin from the preparation, and improved in the stability of indomethacin in the preparation.

DISCLOSURE OF THE INVENTION

As a result of extensive studies in an attempt to solve the above-described problems, the inventors of this invention found that when indomethacin exists as α-form crystals in a vehicle of a transdermal absorption preparation, its percutaneous absorption could be increased, and the stability of indomethacin could also be improved. This finding led them to accomplish the invention.

That is, the invention relates to a transdermal absorption preparation containing α-form crystals of indomethacin in a vehicle.

In the invention, indomethacin may be present as α-form crystals in the vehicle. In other words, it is not absolutely necessary to use α-form crystals of indomethacin as a raw material for the preparation. Instead, a powder of indomethacin, or indomethacin in any of the three crystal forms may be used as a raw material for the preparation. Nor is it necessary for all of indomethacin to exist as α-form crystals in the vehicle.

The dosage form of the transdermal absorption preparation that achieves the effect of the invention includes, for example, a liquid, a cream, an ointment, a gel, a patch, and an aerosol. However, these dosage forms are not limitative, and any dosage form usually applicable to the integument can be used.

To make indomethacin existent as α-form crystals in the vehicle, particular conditions are required. That is, the pH of the vehicle, the amount of water blended, the type and amount of addition of a solvent for suspending indomethacin, the amount of indomethacin incorporated, the temperature during production, the rate of stirring during mixing, and the viscosity of the vehicle are of importance. Especially, the pH of the vehicle, the amount of water blended, the type and amount of addition of the solvent, and the amount of indomethacin incorporated are important.

The pH of the vehicle is 3.5 to 5.5, preferably 4.0 to 5.0. At pH of lower than 3.5, γ-form crystals are liable to occur. At pH of higher than 5.5, the amount of indomethacin dissolved increases, thus making it difficult to obtain α-form crystals.

The amount of water blended is 30 to 90% by weight, preferably 40 to 80% by weight, in the vehicle. If the amount of water blended is less than 30% by weight, the amount of indomethacin dissolved in the solvent will increase. If the amount of water blended is more than 90% by weight, γ-form crystals are liable to occur, thus making it difficult to obtain α-form crystals.

There is no limitation on the solvent for suspending indomethacin. Its examples are ethanol, propanol, isopropanol, propylene glycol, butylene glycol, polyethylene glycol, polyoxyethylene sorbitan fatty acid ester, polyoxyethylene hydrogenated castor oil, polyoxyethylene glycol fatty acid ester, polyoxyethylene polyoxypropyl alkyl ether, polyoxyethylene glycol ether, sorbitan fatty acid ester, and glycerin fatty acid ester. These solvents can be used alone or in combination of two or more. Preferably, propanol, isopropanol, propylene glycol, butylene glycol, and polyethylene glycol can be used alone or in combination of two or more. The amount of the solvent incorporated is 1 to 30% by weight, preferably 5 to 25% by weight, in the vehicle. If the amount of the suspending solvent incorporated is less than 1% by weight, γ-form crystals are liable to occur. If this amount is more than 30% by weight, the amount of indomethacin dissolved in the solvent increases, thus making it difficult to obtain α-form crystals.

In addition to the amount of water incorporated in the vehicle and the amount of the suspending solvent incorporated in the vehicle, the mixing ratio of the water and the suspending solvent is important. If expressed as the weight ratio, the mixing ratio is 70:30 to 95:5, preferably 80:20 to 90:10. At a mixing ratio of 70:30 to 95:5, α-form crystals of indomethacin are easy to be obtained.

The amount of indomethacin incorporated is 1 to 40% by weight, preferably 2 to 20% by weight, based on the suspension, and 0.1 to 2% by weight, preferably 0.3 to 1% by weight, in the vehicle. If the amount of indomethacin incorporated is less than 1% by weight based on the suspension, and less than 0.1% by weight in the vehicle, the dissolution rate of indomethacin increases. If the amount of indomethacin incorporated is more than 40% by weight based on the suspension, and more than 2% by weight in the vehicle, γ-form crystals are liable to occur, thus making it difficult to obtain α-form crystals.

The temperature during production of the vehicle is 5° C. or higher, preferably 10° C. or higher. If the temperature is lower than 5° C., the solubility of indomethacin in the vehicle declines, and γ-form crystals are liable to occur, thus making it difficult to obtain α-form crystals.

The stirring rate during mixing differs according to the type of a mixer. When a biaxial kneader is used, for example, the rotational speed of the kneader is 5 to 100 revolutions/min, preferably 10 to 80 revolutions/min. At a kneader rotational speed of 5 to 100 revolutions/min, α-form crystals of indomethacin are easy to be obtained.

The viscosity of the vehicle in a 10% aqueous solution is 2,000 cps or lower, preferably 1,000 cps or lower. At a viscosity of more than 2,000 cps, the degree of freedom of indomethacin in the adhesive mass declines, thus making it difficult to obtain α-form crystals. Furthermore, the diffusion rate of dissolved indomethacin in the vehicle decreases, thus making it difficult to achieve satisfactory percutaneous absorption.

Water-soluble polymers, which can be added, where necessary, to the transdermal absorption preparation of the invention, include, for example, naturally occurring polymers, such as gelatin, alginate, corn starch, tragacanth gum, casein, and pectin; semisynthetic polymers, such as methyl cellulose, ethyl cellulose, hydroxyethyl cellulose, carboxymethyl cellulose, dextrin, and carboxymethyl starch; synthetic polymers, such as polyvinyl alcohol, sodium polyacrylate, methoxyethylene maleic anhydride copolymer, polyvinyl ether, polyvinyl pyrrolidone, carboxyvinylpolymer, and polyacrylic acid. These polymers can be used alone or as a mixture of two or more. The amount of the any of these water-soluble polymers incorporated in the preparation is 30% by weight or less, preferably 15% by weight or less. If this amount is more than 30% by weight, it will become difficult to maintain the form of the preparation.

In the transdermal absorption preparation of the invention, the following synergists may be incorporated, where necessary, in addition to the above-mentioned ingredients: Salicylic esters, such as methyl salicylate, and glycol salicylate, ibuprofen, azulene, azulene sulfonate sodium, glycyrrhetic acid, and glycyrrhizin, as anti-inflammatory analgesics; diphenhydramine, and chlorpheniramine maleate, as antihistaminics; capsicum and its extract, nonylic vanillylamide, and benzyl nicotinate, as rubefacients; ethyl aminobenzoate, lidocaine, and dibucaine, as local anesthetics; tocopherol acetate, biotin, and vitamin B complex, as vitamins; camphor, menthol, and mentha oil, as refreshing agents; and ginger, zingiber siccatum, paeoniae radix, ginseng, angericae radix, and other extracts, as vegetable and animal drug ingredients. In addition, vehicle components or the like, which are usually used to obtain desired dosage forms, can be incorporated.

As means for making indomethacin present as α-form crystals in the vehicle, the addition of a suspension of indomethacin to a water-soluble gel is cited as an example in the case of a patch. The water-soluble gel used here is not limited, if it is one which is crosslinkable, which is formed from a gelable, water-soluble polymer, and which has moderate stickiness depending on external conditions such as temperature. Examples of the water-soluble polymer are naturally occurring polymers, such as gelatin, alginate, corn starch, tragacanth gum, casein, and pectin; semisynthetic polymers, such as methyl cellulose, ethyl cellulose, hydroxyethyl cellulose, carboxymethyl cellulose, dextrin, and carboxymethyl starch; synthetic polymers, such as polyvinyl alcohol, sodium polyacrylate, methoxyethylene maleic anhydride copolymer, polyvinyl ether, polyvinyl pyrrolidone, carboxyvinylpolymer, and polyacrylic acid. These polymers can be used alone or in combination of two or more. To the resulting vehicle, water-soluble polymers other than those mentioned above, stabilizers, humectants, pH-adjustors, synergists, and if desired, crosslinking agents may be added to make the preparation of the invention.

Confirmation of α-form crystals of indomethacin in the preparation can be performed by visual inspection with a polarizing microscope which will be shown later in a Test Example, infrared analysis, X-ray analysis, differential thermal analysis, and a combination of any of them (N. Kananiwa, Seiyaku Kojo, 5, 9, 738–741, 1985).

BEST MODE FOR CARRYING OUT THE INVENTION

The present invention will now be described more concretely by way of Examples and Test Examples, but the scope of the invention is not limited by these examples.

EXAMPLE 1

Patch

| Ingredient | Amount incorporated, wt. % |
|---|---|
| Indomethacin | 1.0 |
| Tocopherol acetate | 3.0 |
| D-sorbitol | 15.0 |
| Carboxyvinylpolymer | 2.0 |
| Polyoxyethylene sorbitan monooleate | 0.5 |
| Propylene glycol | 8.0 |
| Polyacrylic acid | 6.0 |
| Sodium polyacrylate | 3.0 |
| Tartaric acid | 1.5 |
| Ethyl p-hydroxybenzoate | 0.05 |
| Aluminum hydroxide | 0.5 |
| Purified water | 59.45 |

Water was added to polyacrylic acid, D-sorbitol, and carboxyvinylpolymer, and tartaric acid was further added, followed by mixing these materials, to prepare a water-soluble gel. Separately, polyoxyethylene sorbitan monooleate, tocopherol acetate, and ethyl p-hydroxybenzoate were added to propylene glycol. The resulting mixture was heated and dissolved, whereafter aluminum hydroxide, sodium polyacrylate, and indomethacin powder were added. These materials were dispersed uniformly to produce an indomethacin suspension. To the aforementioned water-soluble gel, the indomethacin suspension was added, and these materials were mixed uniformly at room temperature by means of a biaxial kneader (rotational speed: 50 revolutions/min). The pH of the resulting vehicle was 4.5. The resulting vehicle (adhesive mass) was coated onto an unwoven fabric, and a liner was applied thereto. The composite was cut to make a cataplasm.

EXAMPLE 2

Patch

A cataplasm was prepared by the same production method as in Example 1, except that propylene glycol was replaced by propanol.

EXAMPLE 3

Patch

A cataplasm was prepared by the same production method as in Example 1, except that propylene glycol was replaced by polyethylene glycol 400.

EXAMPLE 4

Patch

A cataplasm was prepared by the same production method as in Example 1, except that propylene glycol was replaced by 1,3-butylene glycol.

EXAMPLE 5

Patch

A cataplasm was prepared by the same production method as in Example 1, except that propylene glycol was replaced by polyethylene sorbitan monooleate.

EXAMPLE 6

Cream for External Use

| Ingredient | Amount incorporated, wt. % |
|---|---|
| Indomethacin | 1.0 |
| Middle chain fatty acid triglyceride | 10.0 |
| Diisopropyl adipate | 5.0 |
| Propylene glycol | 12.0 |
| Polyoxyethylene sorbitan monostearate | 6.0 |
| Sorbitan monostearate | 3.0 |
| Glycerin monostearate | 8.0 |
| Citric acid | 0.1 |
| Purified water | 54.9 |

A cream for external use was produced from the above ingredients in accordance with a preparation method for an emulsion.

EXAMPLE 7

Gel

| Ingredient | Amount incorporated, wt. % |
|---|---|
| Indomethacin | 0.5 |
| Polyethylene glycol monostearate | 5.0 |
| Diisopropyl adipate | 3.0 |
| 1,3-Butylene glycol | 8.0 |
| Polyvinyl pyrrolidone | 0.5 |
| Carboxyvinylpolymer | 1.5 |
| Citric acid | 0.1 |
| Denatured ethanol | 30.0 |
| Purified water | 51.4 |

A gel for external use was produced from the above ingredients in accordance with a preparation method for a gel.

EXAMPLE 8

Liquid for External Use

| Ingredient | Amount incorporated, wt. % |
|---|---|
| Indomethacin | 0.75 |
| Diisopropyl adipate | 5.00 |
| Isopropyl myristate | 3.00 |
| Glycerin | 2.00 |
| Polyoxyethylene alkyl ether | 3.00 |
| Citric acid | 0.10 |
| Denatured ethanol | 45.00 |
| Purified water | 41.15 |

The above ingredients were stirred, and dissolved uniformly to obtain a liquid for external use.

EXAMPLE 9

Aerosol

| Ingredient | Amount incorporated, wt. % |
|---|---|
| Indomethacin | 0.4 |
| Polyethylene sorbitan tristearate | 1.2 |
| Diisopropyl adipate | 2.0 |
| 1,3-Butylene glycol | 1.2 |
| Citric acid | 0.1 |
| Ethanol | 18.0 |
| Purified water | 17.1 |
| Isopentane | 10.0 |
| Liquefied petroleum gas | 3.0 |
| Dimethyl ether | 47.0 |

An aerosol for external use was produced from the above ingredients in accordance with a preparation method for an aerosol.

The resulting preparation was subjected to the following test, in which an indomethacin-containing commercially available cataplasm (GESIC HAP, Sato Pharmaceutical Co., Ltd.) was used as a control.

Test Example 1

Confirmation of Crystal Form of Indomethacin

The preparation of Example 1 and the preparation as the control were each adhered onto a slide glass, and photographed using a polarizing microscope system (produced by NIKON). The results are shown in FIGS. 1 and 2.

The polarizing microscopic photograph of the preparation of Example 1 shown in FIG. 1 clearly demonstrates the presence of needle-like α-form crystals, while the photograph of the control shown in FIG. 2 clearly demonstrates the presence of platy γ-form crystals.

Test Example 2

Permeation Test on the Removed Skin From Rat

The test was conducted in accordance with the descriptions of E. Manabe et al., Int. J. Pharm., 129, 211–221 (1996).

To a pealed abdominal skin of a male hairless rat, the preparation (each of Example 1 and the control) cut to a size of 2 cm in diameter was applied. The resulting specimen was mounted on a horizontal diffusion cell, and 3 ml of phosphate buffer (pH 7.4) was placed on a receiver side. The receiver liquid was sampled over time in a constant amount, and the amount of indomethacin that had permeated was measured by liquid chromatography. The results are shown in FIG. 3.

The cataplasm of Example 1 containing indomethacin as α-form crystals clearly exhibited higher skin permeation than the cataplasm as the control containing indomethacin as γ-form crystals.

Test Example 3

Stability Test

The preparation of Example 1 and the preparation as the control were each placed in pouches in an amount of 5 preparations per pouch, and stored for 8 months at 40° C. and 75% RH. During this period, the stability of indomethacin in the adhesive substance was evaluated.

The results are shown in Table 1.

TABLE 1

|  | Immediately after | 40° C. 75% RH | | |
|---|---|---|---|---|
|  |  | 3 months | 6 months | 8 months |
| Example 1 | 99.5 | 103.8 | 98.6 | 101.6 |
|  | 100.4 | 101.7 | 98.1 | 103.3 |
|  | 100.4 | 102.3 | 101.9 | 103.8 |
| Control | 101.7 | 91.4 | 88.6 | 81.6 |
|  | 100.7 | 92.3 | 88.1 | 83.3 |
|  | 101.2 | 93.3 | 89.9 | 83.8 |

Unit: % of the charge (measured by liquid chromatography)

The cataplasm of Example 1 containing indomethacin as α-form crystals maintained the stability of indomethacin even after 8 months of storage under the storage conditions of 40° C. and 75% RH. On the other hand, the cataplasm as the control containing indomethacin as γ-form crystals was demonstrated to be lower in stability.

BRIEF DESCRIPTION OF THE DRAWINGS

FIG. 3 is a view showing the results of a permeation test on the removed skin from rat with the cataplasms of Example 1 and the control.

INDUSTRIAL APPLICABILITY

Figure 1:
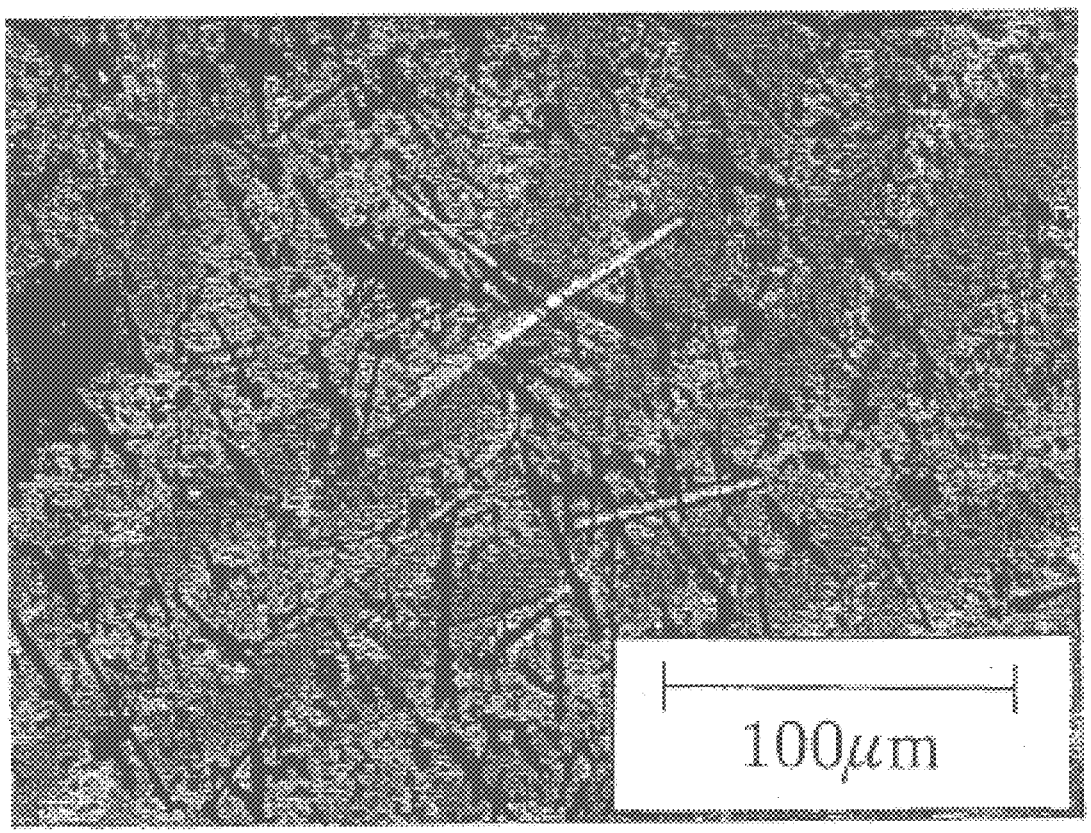
FIG. 1 is a photograph of the cataplasm of Example 1 taken with a polarizing microscope system.
Figure 2:
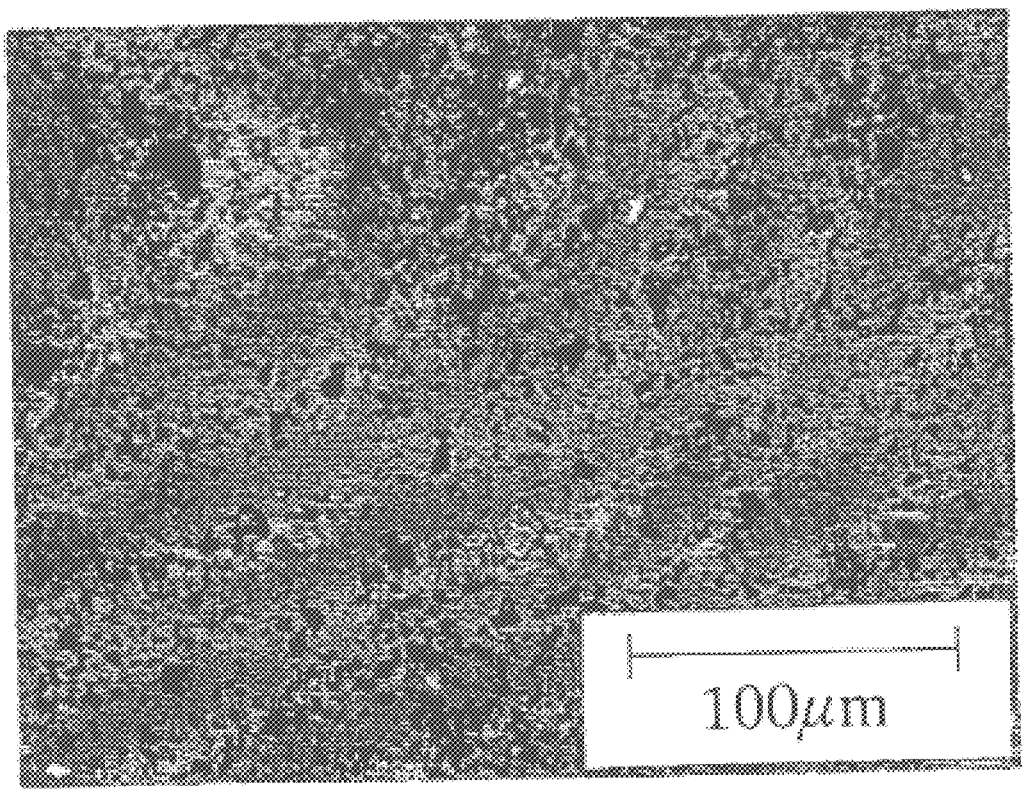
FIG. 2 is a photograph of the cataplasm as the control taken with a polarizing microscope system.

The present invention can provide an indomethacin-containing transdermal absorption preparation increased in the percutaneous absorption of indomethacin from the preparation, and improved in the stability of indomethacin in the preparation.

What is claimed is:

1. An indomethacin-containing patch comprising 1 to 40% by weight indomethacin in α-form crystals in suspension in a vehicle wherein said vehicle comprises water, indomethacin and solvent, and wherein:

(a) the vehicle has a pH of 4.0 to 5.0, (b) said water is present in the vehicle in an amount of 30 to 90% by weight, (c) said indomethacin is present in the vehicle in an amount of 0.1 to 2% by weight, and (d) the amount of said water incorporated into the vehicle to the amount of an indomethacin-suspending solvent incorporated into the vehicle is 70:30 to 95:5 (wt by wt).

2. The patch of claim 1, wherein the amount of the indomethacin-suspending solvent incorporated in the vehicle is 1 to 30% by weight.

3. The patch of claim 1, wherein the indomethacin-suspending solvent is one or more compounds selected from the group consisting of propanol, isopropanol, propylene glycol, butylene glycol and polyethylene glycol.

* * * * *